(12) United States Patent
Oshida et al.

(10) Patent No.: US 10,549,333 B2
(45) Date of Patent: Feb. 4, 2020

(54) MEDICAL NEEDLE MANUFACTURING METHOD, MEDICAL NEEDLE MANUFACTURING APPARATUS, AND MEDICAL NEEDLE

(71) Applicant: TERUMO KABUSHIKI KAISHA, Shibuya-ku (JP)

(72) Inventors: Masatoshi Oshida, Shizuoka (JP); Kenta Goto, Kamanashi (JP); Naoki Uchida, Yamanashi (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 274 days.

(21) Appl. No.: 15/332,069

(22) Filed: Oct. 24, 2016

(65) Prior Publication Data
US 2017/0135720 A1    May 18, 2017

(30) Foreign Application Priority Data
Nov. 12, 2015 (JP) ................................. 2015-221728

(51) Int. Cl.
*B21D 41/02* (2006.01)
(52) U.S. Cl.
CPC .................... *B21D 41/02* (2013.01)
(58) Field of Classification Search
CPC ..................................................... B21D 41/02
See application file for complete search history.

(56) References Cited

FOREIGN PATENT DOCUMENTS

| JP | 62-243564 A | 10/1987 |
|----|-------------|---------|
| JP | H02-152465 A | 6/1990 |

OTHER PUBLICATIONS

Office Action (Notice of Reasons for Refusal) dated Aug. 6, 2019, by the Japanese Patent Office in corresponding Japanese Patent Application No. 2015-221728 and an English Translation of the Office Action. (8 pages).

*Primary Examiner* — Larry W Thrower
(74) *Attorney, Agent, or Firm* — Buchanan Ingersoll & Rooney PC (57) ABSTRACT

A medical needle manufacturing method, a medical needle manufacturing apparatus, and a medical needle are disclosed capable of suppressing the generation of a level difference and burrs/flashes in a boundary section between a needle hub and a needle body in an inner peripheral portion of the needle hub. The manufacturing method of a medical needle includes a large-diameter-portion molding step of molding, by a core pin, a large-diameter portion in a proximal portion of a needle body; a core-pin backward-movement step of moving backward the core pin by a predetermined distance relatively to the needle body; and an injection molding step of molding a needle hub by injecting a resin into an injection molding mold.

16 Claims, 6 Drawing Sheets

MEDICAL NEEDLE MANUFACTURING METHOD, MEDICAL NEEDLE MANUFACTURING APPARATUS, AND MEDICAL NEEDLE

CROSS-REFERENCES TO RELATED APPLICATIONS

This application claims priority to Japanese Patent Application No. 2015-221728, filed on Nov. 12, 2015, the entire content of which is incorporated herein by reference.

TECHNICAL FIELD

The present disclosure relates to a medical needle manufacturing method and a medical needle manufacturing apparatus for manufacturing a medical needle having a needle hub fixed to a proximal portion of a needle body by insert molding, and a medical needle.

BACKGROUND DISCUSSION

As a method of manufacturing a medical needle that has a hollow metallic needle body on which a needle tip that can be punctured into a living body is formed, and a resin needle hub which is fixed to a proximal portion of this needle body, there are known a bonding method and an insert molding method. With the bonding method, a needle body and a needle hub are manufactured separately, and the needle body and the needle hub are fixed to each other using an adhesive. On the other hand, with the insert molding method, a needle body is set into an injection molding mold for molding a needle hub and a resin is injected into the injection molding mold, thereby molding the needle hub integrally in a proximal portion of the needle body.

JP-A S62-243564 proposes a method of manufacturing a medical needle by the insert molding method. Specifically, with the manufacturing method of JP-A S62-243564, a core pin is inserted into a needle body from a rear end portion of the needle body, thereby forcibly widening the rear end portion into a flare shape, and a resin is then injected into an injection molding mold, thereby molding a needle hub.

The manufacturing method of JP-A S62-243564 can have a problem that when the core pin is pulled out from a molded article after the injection molding, the needle body proximal portion (flare-shaped portion) returns to an original state by spring back, resulting in the generation of a level difference and burrs/flashes in a boundary section between the needle hub and the needle body in an inner peripheral portion of the needle hub. In particular, when a medical elongated body (for example, a guide wire) is inserted into a medical needle from a proximal side of the medical needle and the level difference and burrs/flashes described above are present, it can be difficult to smoothly insert the medical elongated body.

SUMMARY

A medical needle manufacturing method, a medical needle manufacturing apparatus, and a medical needle are disclosed, which are capable of suppressing the generation of a level difference and burrs/flashes in a boundary section between a needle hub and a needle body in an inner peripheral portion of the needle hub.

In accordance with an exemplary embodiment, the present disclosure provides a manufacturing method of a medical needle provided with a hollow metallic needle body and a resin needle hub fixed to a proximal portion of the needle body, the method including: a large-diameter-portion molding step of molding a large-diameter portion in the proximal portion of the needle body by inserting a core pin of an injection molding mold into the proximal portion and widening the proximal portion; a core-pin backward-movement step of, after the large-diameter-portion molding step, moving backward the core pin by a predetermined distance relatively to the needle body in such a manner that the large-diameter portion springs back; and an injection molding step of, after the core-pin backward-movement step, molding the needle hub by injecting a resin into the injection molding mold while relative positions of the needle body and the core pin are held.

With the manufacturing method of the medical needle of the present disclosure including the abovementioned steps, the large-diameter portion is molded in the proximal portion of the needle body by the core pin, whereby an inner surface shape of the proximal portion is corrected into the shape of the core pin. That is, the inner surface of the needle body can be shaped in accordance with an outer surface shape of the core pin used in molding. Therefore, using the core pin excellent in the roundness of the outer surface shape helps enable the inner surface of the large-diameter portion of the needle body to be superior in roundness to the other portions. Furthermore, the core pin is moved backward by the predetermined distance relatively to the needle body, which has been subjected to the large-diameter-portion molding processing, thereby causing the large-diameter portion to spring back, and the injection molding is then carried out. Due to this, a substantially constant gap is formed between the core pin and the needle body (proximal portion) while a partially large gap due to the difference between the inner surface shape of the needle body and the outer surface shape of the core pin is not generated; therefore, the generation of flashes due to the partial entry of the resin resulting from the injection molding can be suppressed. Moreover, because spring back occurs prior to the injection molding, the needle body does not deform after removing the core pin; therefore, the generation of a level difference between the needle hub, which has been molded, and the needle body and the generation of burrs/flashes within the molded needle hub can be suppressed. Furthermore, the appropriate gap is generated between the core pin and the needle body by the core-pin backward-movement step; therefore, it is easy to release air within the mold to outside via the gap during the injection molding. It is thereby possible to suppress the occurrence of molding failures such as air bubbles and sink marks.

In the aforementioned manufacturing method of the medical needle, the core-pin backward-movement step may include moving backward the core pin relatively to the needle body in such a manner that a gap into which the resin cannot flow is formed between the large-diameter portion and the core pin.

It is thereby possible to help ensure the prevention of the generation of flashes in the proximal portion of the needle body.

In the aforementioned manufacturing method of the medical needle, the core pin may include a large-diameter-portion molding portion for molding the large-diameter portion; and a support portion smaller in a diameter than the large-diameter-portion molding portion, extending from a distal end of the large-diameter-portion molding portion in a distal direction, inserted into the proximal portion of the needle body, and supporting the needle body from inside.

It is thereby relatively easy to set a processing condition width that helps enable the suppression of the generation of flashes to be larger than that in a case, for example, in which the core pin which has a tapered distal insertion portion having a diameter decreasing toward the distal direction is used on a distal side of the large-diameter-portion molding portion.

In the aforementioned manufacturing method of the medical needle, the large-diameter portion may be a flare-shaped portion having a diameter increasing toward a proximal direction. Furthermore, in the aforementioned manufacturing method of the medical needle, the large-diameter portion may be a flare-shaped portion having a diameter increasing toward the proximal direction, and the large-diameter-portion molding portion may be a tapered portion having an outer diameter decreasing toward the distal direction.

In accordance with an exemplary embodiment, the present disclosure provides a medical needle manufacturing apparatus for manufacturing a medical needle provided with a hollow metallic needle body and a resin needle hub fixed to a proximal portion of the needle body, the apparatus including: an injection molding mold including a cavity for molding an outer shape of the needle hub and a core pin for molding an inner shape of the needle hub; an injection section injecting a resin into the injection molding mold; a moving mechanism section axially moving the core pin relatively to the needle body; and a control unit controlling the injection section and the moving mechanism section, wherein the control unit controls the injection section and the moving mechanism section in such a manner to execute: a large-diameter-portion molding step of molding a large-diameter portion in the proximal portion of the needle body by inserting the core pin into the proximal portion and widening the proximal portion; a core-pin backward-movement step of, after the large-diameter-portion molding step, moving backward the core pin by a predetermined distance relatively to the needle body in such a manner that the large-diameter portion springs back; and an injection molding step of, after the core-pin backward-movement step, molding the needle hub by injecting the resin into the injection molding mold while relative positions of the needle body and the core pin are held.

In the aforementioned medical needle manufacturing apparatus, the control unit may exert a control such that the core-pin backward-movement step includes moving backward the core pin relatively to the needle body in such a manner that a gap into which the resin cannot flow is formed between the large-diameter portion and the core pin.

In the aforementioned medical needle manufacturing apparatus, the core pin may include a large-diameter-portion molding portion for molding the large-diameter portion; and a support portion smaller in a diameter than the large-diameter-portion molding portion, extending from a distal end of the large-diameter-portion molding portion in a distal direction, inserted into the proximal portion of the needle body, and supporting the needle body from inside.

In accordance with an exemplary embodiment, a medical needle is disclosed, which includes: a hollow metallic needle body; and a resin needle hub fixed to a proximal portion of the needle body, wherein the medical needle includes a large-diameter portion in the proximal portion of the needle body, an inner peripheral shape of the large-diameter portion being closer to a perfect circle than inner peripheral shapes of portions, other than the large-diameter portion, of the needle body, and in the proximal portion of the needle body fixed to the needle hub, there is substantially no level difference between an inner surface of the large-diameter portion and an inner surface of the needle hub to which a proximal surface of the large-diameter portion is adjacent.

The medical needle manufacturing method, the medical needle manufacturing apparatus, and the medical needle of the present disclosure can suppress the generation of a level difference and burrs/flashes in a boundary section between the needle hub and the needle body in the inner peripheral portion of the needle hub.

DETAILED DESCRIPTION

A medical needle manufacturing method, a medical needle manufacturing apparatus, and a medical needle according to the present disclosure will be described hereinafter with reference to the accompanying drawings while taking a preferred embodiment as an example.

Figure 1:
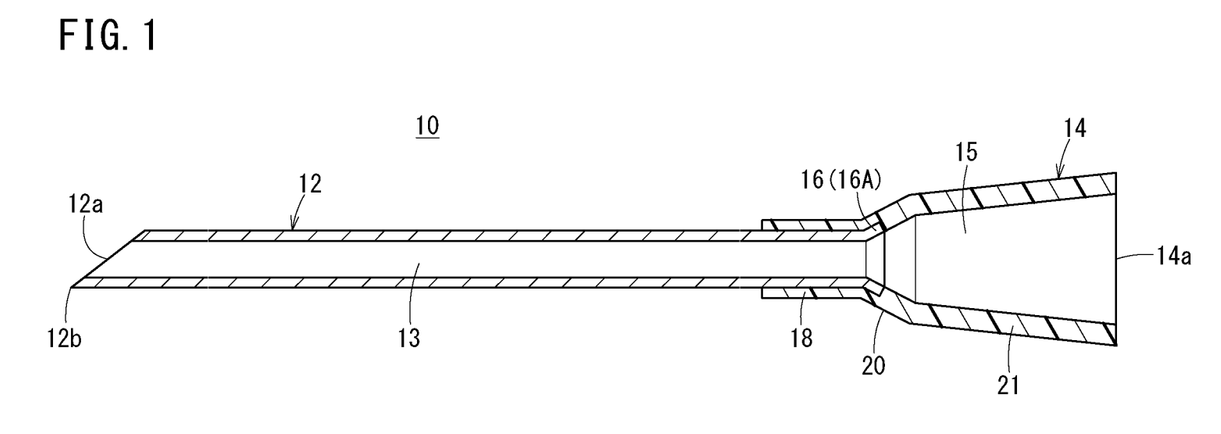
FIG. 1 is a cross-sectional view of a medical needle manufactured by a medical needle manufacturing method according to an embodiment of the present disclosure.

A medical needle 10 shown in FIG. 1 is configured as, for example, a puncture needle that is a constituent element of an introducer kit for use when a catheter is inserted into a blood vessel, or an inner needle that is a constituent element of an indwelling needle punctured into a patient's skin and indwelling therein in order to administer an infusion or the like to a patient.

As shown in FIG. 1, the medical needle 10 is provided with a hollow needle body 12 (cannula) that can be punctured into a skin of a living body, and a needle hub 14 that is fixed to a proximal portion of the needle body 12.

The needle body 12 is a metallic hollow cylindrical tube where a lumen 13 that axially penetrates the needle body 12 is formed. This lumen 13 communicates with a distal opening of the needle body 12. An edge surface 12a inclined with respect to an axis is provided in a distal portion of the needle body 12, and a sharp needle tip 12b is provided in an extreme distal portion of the needle body 12 (distal end of the edge surface 12a).

In the proximal portion of the needle body 12, there is provided, as a large-diameter portion 16 having a diameter increased to be larger than that of the other portions (portions, which are closer to a distal side than the proximal portion, of the needle body 12), a flare-shaped portion 16A having an outer diameter and an inner diameter increased into a tapered fashion toward a proximal direction. Note that in the needle body 12, a section between a proximal end of the edge surface 12a and a distal end of the flare-shaped portion 16A is formed such that an outer shape thereof is a constant, straight shape.

The needle body 12 exhibits appropriate rigidity such that the needle body 12 is not largely bent when being punctured into the skin of the living body. Examples of a metallic material that constitutes such a needle body 12 include stainless steel, a cobalt chrome alloy, aluminum or an aluminum alloy, and titanium or a titanium alloy.

The needle hub 14 can be a hollow resin member having a lumen that axially penetrates the needle hub 14 and is provided in the proximal portion of the needle body 12 by insert molding. A lumen 15 of the needle hub 14 communicates with the lumen 13 of the needle body 12 and has an opening as a proximal opening portion 14a on a proximal surface of the needle hub 14.

A distal cylindrical portion 18 that constitutes a distal side region of the needle hub 14 is closely fixed to an outer peripheral surface of the proximal portion of the needle body 12. An extreme distal portion of the needle hub 14 is located to be closer to the distal side than the flare-shaped portion 16 of the needle body 12. In the needle hub 14, an inclined portion 20 having an inner diameter and an outer diameter increasing toward the proximal direction is formed on a proximal side of the distal cylindrical portion 18. An inner surface of this inclined portion 20 and an inner surface of the flare-shaped portion 16A are adjacent to each other substantially without any level difference. A body section 21 having an inner diameter and an outer diameter increasing toward the proximal direction at a gradient smaller than that of the inclined portion 20 is formed on the proximal side of the inclined portion 20. The medical needle 10 has the large-diameter portion 16 in the proximal portion of the needle body 12, and an inner peripheral shape of the large-diameter portion 16 is closer to a perfect circle than inner peripheral shapes of the portions of the needle body 12 other than the large-diameter portion 16; the medical needle 10 is formed such that in the proximal portion of the needle body 12 fixed to the needle hub 14, there is substantially no level difference between the inner surface of the large-diameter portion 16 of the lumen 13 and the inner surface of the inclined portion 20 of the needle hub 14 to which a proximal surface of the large-diameter portion 16 is adjacent.

Examples of a resin material that constitutes the needle hub 14 can include thermoplastic resins such as polypropylene, polystyrene, polycarbonate, polyamide, polysulfone, polyarylate, and methacrylate-butylene-styrene copolymer.

Next, referring to FIG. 2, a manufacturing apparatus 22 for manufacturing the abovementioned medical needle 10 will be described.

This manufacturing apparatus 22 is provided with an injection molding mold 24, an injection section 26, a moving mechanism section 28, and a control unit 30, and is configured to mold the needle hub 14 in the proximal portion of the needle body 12 by insert molding.

The injection molding mold 24 is provided with a female mold 34 having a cavity 32 that is a recessed portion for molding an outer surface shape of the needle hub 14, and a male mold 38 having a core pin 36 for molding an inner surface shape of the needle hub 14 (portion closer to the proximal side than the needle body 12). In a state in which the core pin 36 has been disposed within the female mold 34, a gap (molding space 40) corresponding to a shape of the needle hub 14 to be molded is formed between the cavity 32 and the core pin 36.

The cavity 32 of the female mold 34 has a first molding section 42 that molds an outer surface shape of the distal cylindrical portion 18 of the needle hub 14, a second molding section 44 that molds an outer surface shape of the inclined portion 20 of the needle hub 14, and a third molding section 46 that molds an outer surface shape of the body section 21 of the needle hub 14. Furthermore, a first insertion hole 48 into which the needle body 12 is inserted is formed on one end side of the female mold 34, while a second insertion hole 50 into which the core pin 36 is inserted is formed on the other end side of the female mold 34.

Figure 2:
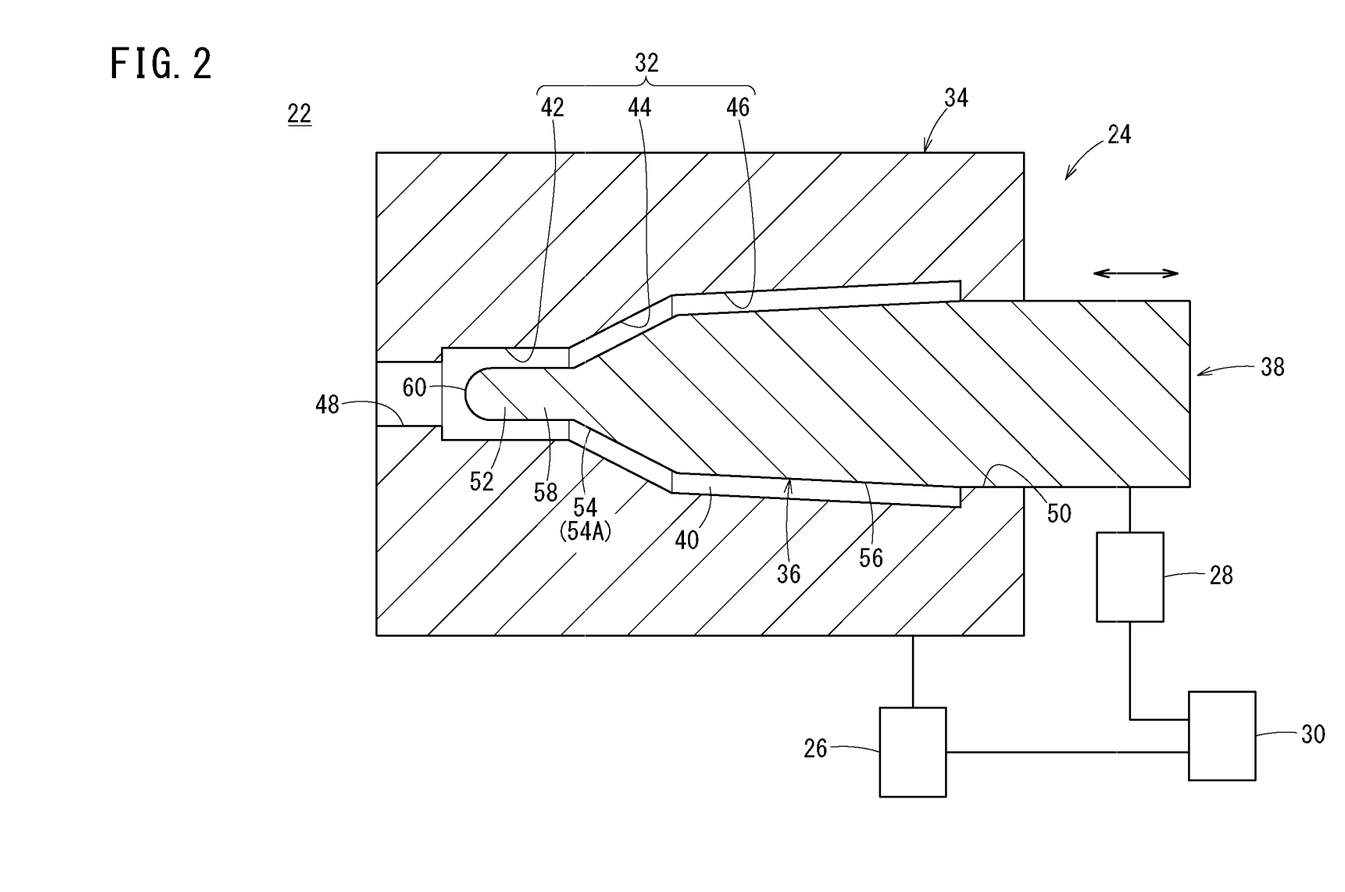
FIG. 2 is a schematic diagram of a medical needle manufacturing apparatus according to the present embodiment of the present disclosure.

Note that although not shown in FIG. 2, the female mold 34 is composed by a plurality of separable molds so that a molded article obtained by the injection molding can be unloaded from the female mold 34.

The core pin 36 has a distal insertion portion 52 which is inserted into the proximal portion of the needle body 12, a tapered portion 54A (large-diameter-portion molding portion 54) that is formed adjacent to a proximal side of the distal insertion portion 52 and having an outer shape tapered toward the distal direction, and a body molding portion 56 that is formed adjacent to a proximal side of this tapered portion 54A and that molds an inner surface shape of the body section 21 of the needle hub 14.

In the present embodiment, the distal insertion portion 52 has a columnar straight portion 58 (support portion) extending from a distal end of the tapered portion 54A in the distal direction with an outer diameter thereof kept substantially constant, and a spherical distal end 60 provided on a distal end of the straight portion 58. The outer diameter of the straight portion 58 is substantially equal to the inner diameter of the needle body 12; strictly, however, the outer diameter thereof is slightly smaller than the inner diameter of the needle body 12. Therefore, in a state in which the distal insertion portion 52 has been inserted into the proximal portion of the needle body 12, a very small gap is formed between an outer peripheral surface of the straight portion 58 and an inner peripheral surface of the needle body 12 to such an extent that air can enter the gap but the resin (molten resin) used for the injection molding cannot enter the gap.

The tapered portion 54A of the core pin 36 is a portion that constitutes a large-diameter-portion molding portion 54 for molding the flare-shaped portion 16A in the proximal portion of the needle body 12 in a flare processing step (large-diameter-portion molding step), to be described later, and that molds an inner surface shape of the inclined portion 20 of the needle hub 14 in an injection molding step, to be described later. An angle of an outer surface of the large-diameter-portion molding portion 54 with respect to an axis of the core pin 36 is set to, for example, 0° to 90°. The angle is set preferably, for example, to 5° to 60°, more preferably 10° to 45°. Note that the angle of the outer shape is assumed as an angle formed between two visible lines in a sagittal section that includes a center line of the large-diameter-portion molding portion 54. A state in which the angle of the outer shape of the large-diameter-portion molding portion 54 is 0° indicates a case where the two visible lines are parallel. When the angle of the outer surface of the large-diameter-portion molding portion 54 is greater than 0°, the large-diameter-portion molding portion 54 has a form of the tapered portion 54A as in the present embodiment. In accordance with an exemplary embodiment, when the angle of the outer surface of the large-diameter-portion molding portion 54 is 0°, the large-diameter-portion molding portion 54 has a form of a straight large-diameter portion which is larger in an outer diameter than the distal insertion portion 52 and which has an outer diameter that is constant axially. The diameter of the straight large-diameter portion is set to be larger than the set inner diameter of the needle body 12 by, for example, 20 μm to 40 μm.

In FIG. 2, the injection section 26 is configured to inject the resin (molten resin) into the molding space 40 of the injection molding mold 24 via an injection passage (not shown). This injection section 26 may be configured similarly to an injection unit of a well-known injection molding machine.

The moving mechanism section 28 is configured to axially move forward and backward the male mold 38 (core pin 36) relatively to the female mold 34. A drive source of the moving mechanism section 28 is not limited a specific one and may be, for example, a cylinder device, a linear motor or a rotary motor. Hereinafter, movement of the core pin 36 in the distal direction will be also referred to as "forward movement/move(d) forward" and movement of the core pin 36 in the proximal direction will be also referred to as "backward movement/move(d) backward".

The control unit 30 controls the injection section 26 and the moving mechanism section 28 in order to carry out the flare processing step, the core-pin backward-movement step, and the injection molding step, to be described later. The control unit 30 may be a dedicated computer provided with a memory that stores a program for executing these steps and an arithmetic processing unit or may be a general-purpose computer into which the program has been installed.

Next, a manufacturing method of the medical needle 10 according to the present embodiment will be described while referring to a relation thereof with the action of the manufacturing apparatus 22 configured as described above. The manufacturing method includes the flare processing step (large-diameter-portion molding step), the core-pin backward-movement step, and the injection molding step as follows.

Figure 3A:
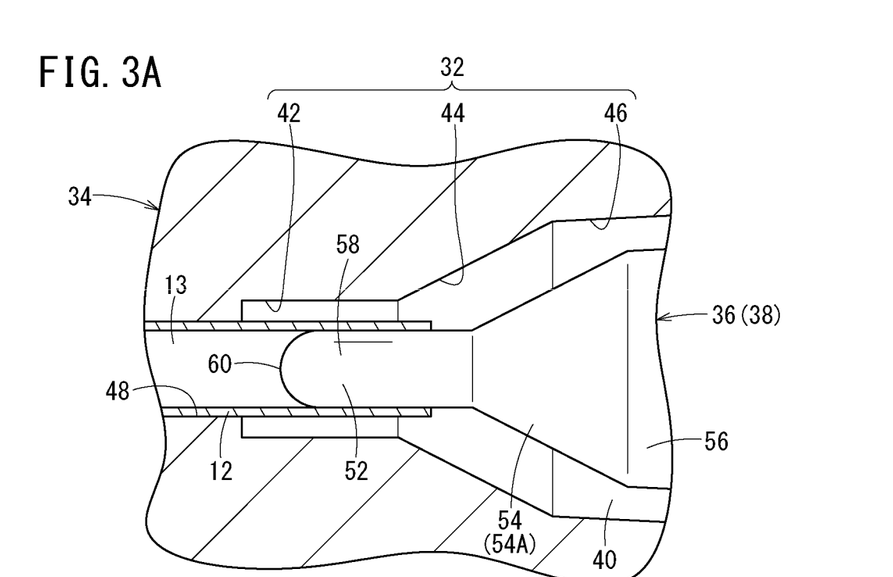
FIG. 3A is a first explanatory diagram of a flare processing step according to an embodiment of the present disclosure.

Prior to the flare processing step, the proximal side of the needle body 12 is inserted into the first insertion hole 48 of the female mold 34, as shown in FIG. 3A. In this case, in a state in which the proximal portion of the needle body 12 has protruded into the cavity 32 of the female mold 34 by a predetermined length, fixing means (not shown) fixes the needle body 12 to the female mold 34. Under the drive action of the moving mechanism section 28 (see FIG. 2), the core pin 36 is moved forward, thereby inserting the distal insertion portion 52 of the core pin 36 into the proximal portion of the needle body 12, as shown in FIG. 3A.

Figure 3B:
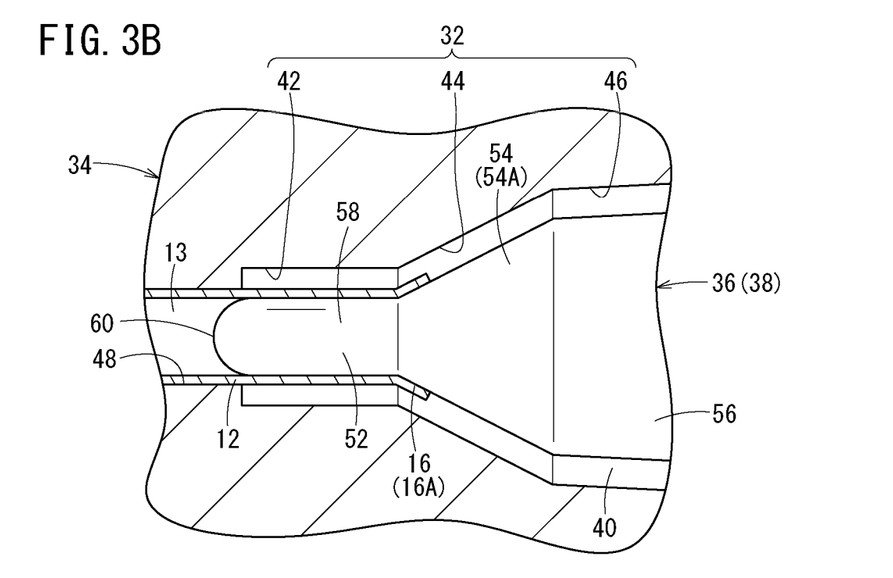
FIG. 3B is a second explanatory diagram of the flare processing step according to an embodiment of the present disclosure.

In the flare processing step, the proximal portion of the needle body 12 is widened as the core pin 36 is moved forward, thereby molding the flare-shaped portion 16A in the proximal portion, as shown in FIG. 3B. That is, for example, the tapered portion 54A of the core pin 36 forcibly widens the proximal portion of the needle body 12 from inside to outside as the core pin 36 is moved forward, thereby molding the proximal portion of the needle body 12 into a flare shape with a plastic deformation involved in the molding. The flare-shaped portion 16A when the molding is completed has a shape that matches an outer surface shape of the tapered portion 54A of the core pin 36. At this time, a forward movement amount by which the core pin 36 is moved forward is preferably, for example, 0.1 mm to 0.3 mm. The forward movement amount can be controlled by a fixed position at which the needle body 12 is fixed into the mold, and a set value and a set movement amount of the core pin 36.

When the core pin 36 has the abovementioned straight large-diameter portion as an alternative to the tapered portion 54A, the proximal portion of the needle body 12 is widened as the core pin 36 is moved forward, whereby a large-diameter straight portion having a constant outer diameter is molded axially in the proximal portion of the needle body 12 as another form of the large-diameter portion 16.

Figure 4:
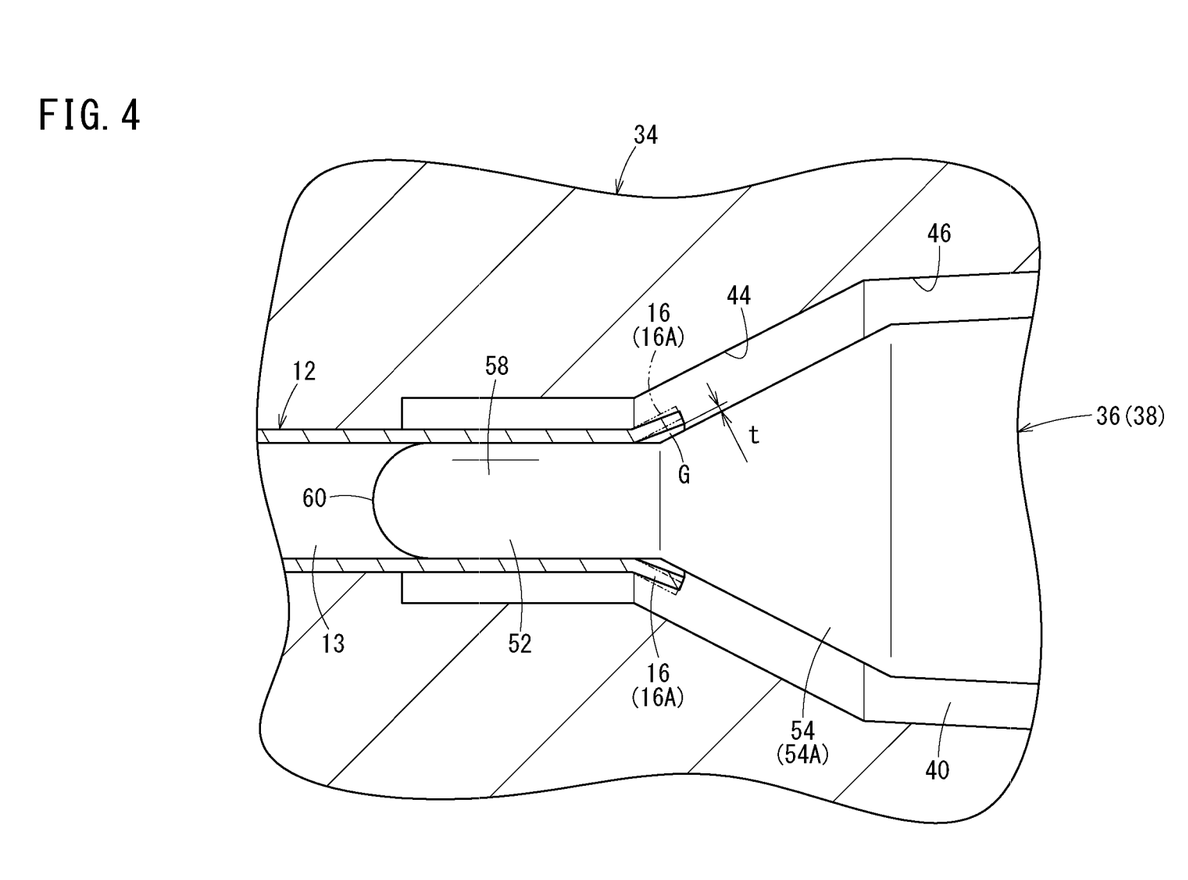
FIG. 4 is an explanatory diagram of a core-pin backward-movement step.

The core-pin backward-movement step is then carried out. In the core-pin backward-movement step, the core pin 36 is moved backward by a predetermined distance relatively to the needle body 12 in such a manner that the flare-shaped portion 16A springs back. Specifically, for example, under the drive action of the moving mechanism section 28 (see FIG. 2), the core pin 36 is moved backward slightly by the predetermined distance relatively to the needle body 12, as shown in FIG. 4. A backward movement distance of the core pin 36 necessary for the flare-shaped portion 16A to spring back is, for example, approximately 0.01 mm to 0.1 mm, depending on conditions including a material and the outer diameter of the needle body 12, a wall thickness, and the forward movement amount. The backward movement distance is preferably, for example, approximately 0.03 mm to 0.08 mm, more preferably, approximately 0.05 mm to 0.07 mm.

Moving the core pin 36 backward in this way causes the occurrence of spring back to the flare-shaped portion 16A. That is, a deformation of the proximal portion of the needle body 12 in the flare processing step is mostly the plastic deformation but partially an elastic deformation. Due to this, when the core pin 36 is moved backward after the flare processing step, the diameter of the flare-shaped portion 16A is slightly decreased by an elastic restoring force. In FIG. 4, the flare-shaped portion 16A before the spring back is indicated by a virtual line. In the core-pin backward-movement step, an inner peripheral shape of the flare-shaped portion 16A is closer to a perfect circle than inner peripheral shapes of the portions of the needle body 12 other than the flare-shaped portion 16A. When the large-diameter straight portion is molded in the proximal portion of the needle body 12 as an alternative to the flare-shaped portion 16A, spring back also occurs to the large-diameter straight portion by the core-pin backward-movement step.

In this case, in the core-pin backward-movement step of the present embodiment, the core pin 36 is moved backward relatively to the needle body 12 so as to form a very small gap G between an inner peripheral surface of the flare-shaped portion 16A and an outer peripheral surface of the core pin 36 (tapered portion 54A) to such an extent that the resin cannot flow into the very small gap G. The gap G is an annular space. A magnitude t of the gap G (distance between a proximal edge of the flare-shaped portion 16A and the tapered portion 54A in a normal direction of the tapered portion 54A) is preferably, for example, equal to or smaller than 10 μm, depending on injection molding conditions. As a result, it is possible to create a state in which there is no flashes and there is substantially no level difference between the inner surface of the needle hub 14 and the inner surface of the needle body 12.

Figure 5:
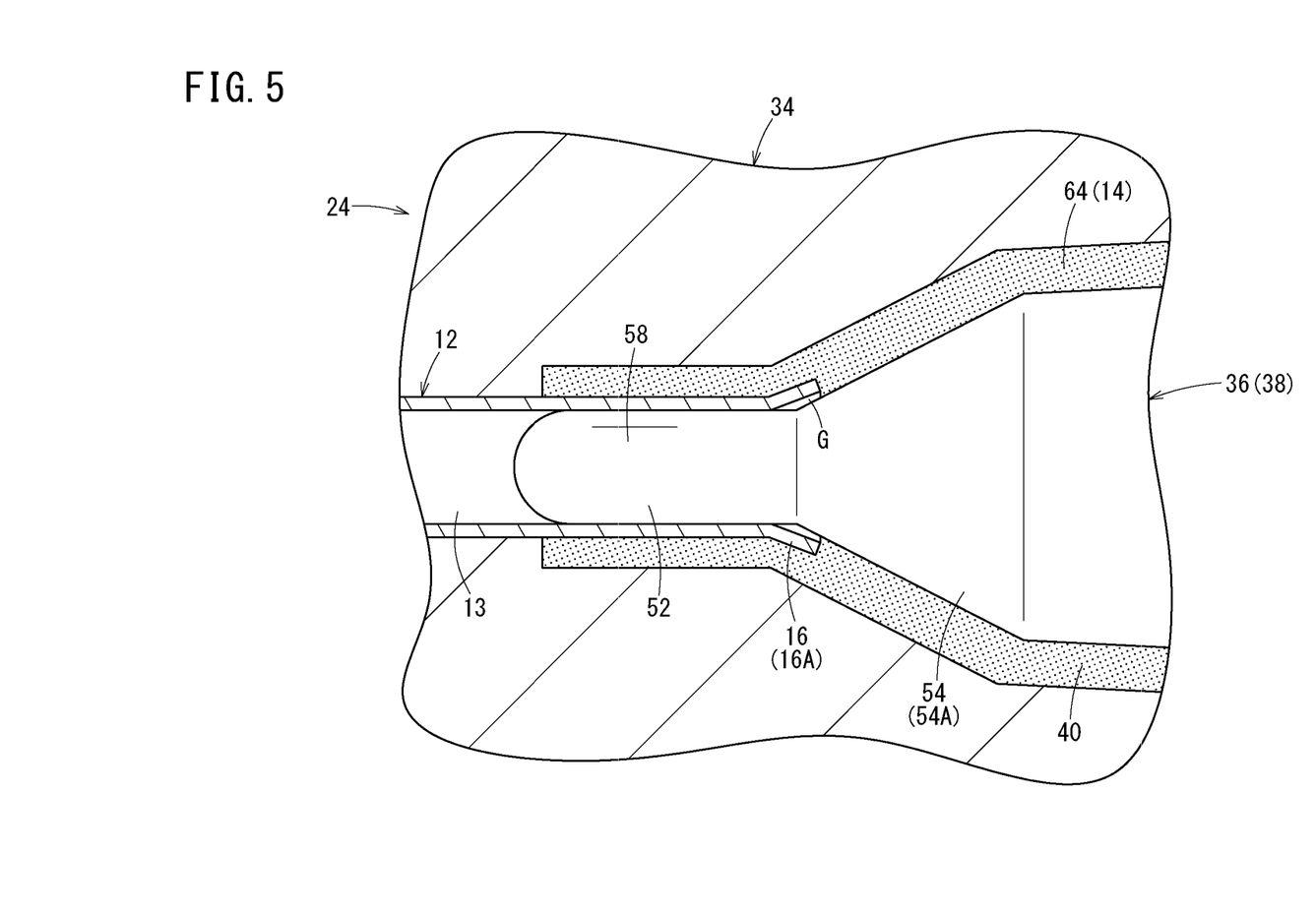
FIG. 5 is an explanatory diagram of an injection molding step.

The injection molding step is then carried out. In the injection molding step, the resin is injected into the injection molding mold 24 (molding space 40) while relative positions of the needle body 12 and the core pin 36 are held, thereby insert-molding the needle hub 14, as shown in FIG. 5. Specifically, for example, by injecting a resin 64 (molten resin) into the molding space 40 formed between the cavity 32 and the core pin 36, the resin 64 flows within the molding space 40 and the molding space 40 is filled with the resin.

In this case, the flare-shaped portion 16A of the needle body 12 which has been molded by the tapered portion 54A of the core pin 36 has an inner surface shape which substantially matches the outer surface shape of the tapered portion 54A even after the spring back caused by the core-pin backward-movement step. Due to this, and since a gap is not formed into which the resin 64 can flow during the injection molding between the needle body 12 and the tapered portion 54A, the generation of flashes that may result from the injection molding can be suppressed.

Furthermore, in the injection molding step, the very small gap G is formed between the inner peripheral surface of the flare-shaped portion 16A and the outer peripheral surface of the tapered portion 54A, and a very small gap is also formed between an outer peripheral surface of the distal insertion portion 52 and the inner peripheral surface of the needle body 12 which faces the outer peripheral surface. Due to this, air which has been present in the molding space 40 can move to the lumen 13 of the needle body 12 communicating with outside via these gaps. Therefore, the occurrence of molding failures such as air bubbles and sink marks can be suppressed.

When the needle hub 14 has been molded by the injection molding step, the core pin 36 is then moved backward in the presence of the drive operation of the moving mechanism section 28 (see FIG. 2) and the needle hub 14 which has been integrated with the needle body 12 is unloaded from the injection molding mold 24. In this case, the flare-shaped portion 16A has already sprung back (the diameter thereof has already been decreased) by the abovementioned core-pin backward-movement step; therefore, the diameter of the flare-shaped portion 16A is not decreased further when the core pin 36 is moved backward after the injection molding.

Therefore, the generation of the level difference between the needle hub 14 which has been molded and the needle body 12 (level difference caused by the inward protrusion of the flare-shaped portion 16A relative to the inner surface of the inclined portion 20) within the needle hub 14 can be suppressed. Furthermore, the generation of burrs/flashes caused by the spring back (flashes formed by peeling off an inner peripheral portion of the inclined portion 20 by the proximal portion of the flare-shaped portion 16A when the flare-shaped portion 16A springs back) can be suppressed.

As described so far, with the manufacturing method of the medical needle 10 according to the present embodiment, the core pin 36 is used to perform flare processing on the proximal portion of the needle body 12, whereby the inner surface shape of the proximal portion thereof is corrected into the shape of the core pin 36. Due to this, a gap is not formed into which the resin 64 can flow between the core pin 36 and the needle body 12 (proximal portion), therefore, the generation of flashes that may result from the injection molding can be suppressed.

Furthermore, with the present manufacturing method, the core pin 36 is moved backward by the predetermined distance relatively to the needle body 12, which has been subjected to the flare processing, thereby causing the flare-shaped portion 16A to spring back, and the injection molding is then carried out. Due to this, the generation of the level difference between the needle hub 14, which has been molded and the needle body 12 and the generation of burrs/flashes within the molded needle hub 14 can be suppressed.

Moreover, the appropriate gap G is generated between the core pin 36 and the needle body 12 by the core-pin backward-movement step; therefore, it is relatively easy to release the air within the mold to outside via the gap G during the injection molding, thereby suppressing the occurrence of molding failures such as air bubbles and sink marks.

In the core-pin backward-movement step, in particular, the core pin 36 is moved backward relatively to the needle body 12 so as to form the gap G into which the resin cannot flow between the flare-shaped portion 16A and the core pin 36. It is thereby possible to help ensure the prevention of the generation of flashes in the proximal portion of the needle body 12.

The abovementioned effects derived from the present manufacturing method can be similarly obtained even when the large-diameter straight portion is molded in the proximal portion of the needle body 12 as an alternative to the flare-shaped portion 16A.

Figure 6:
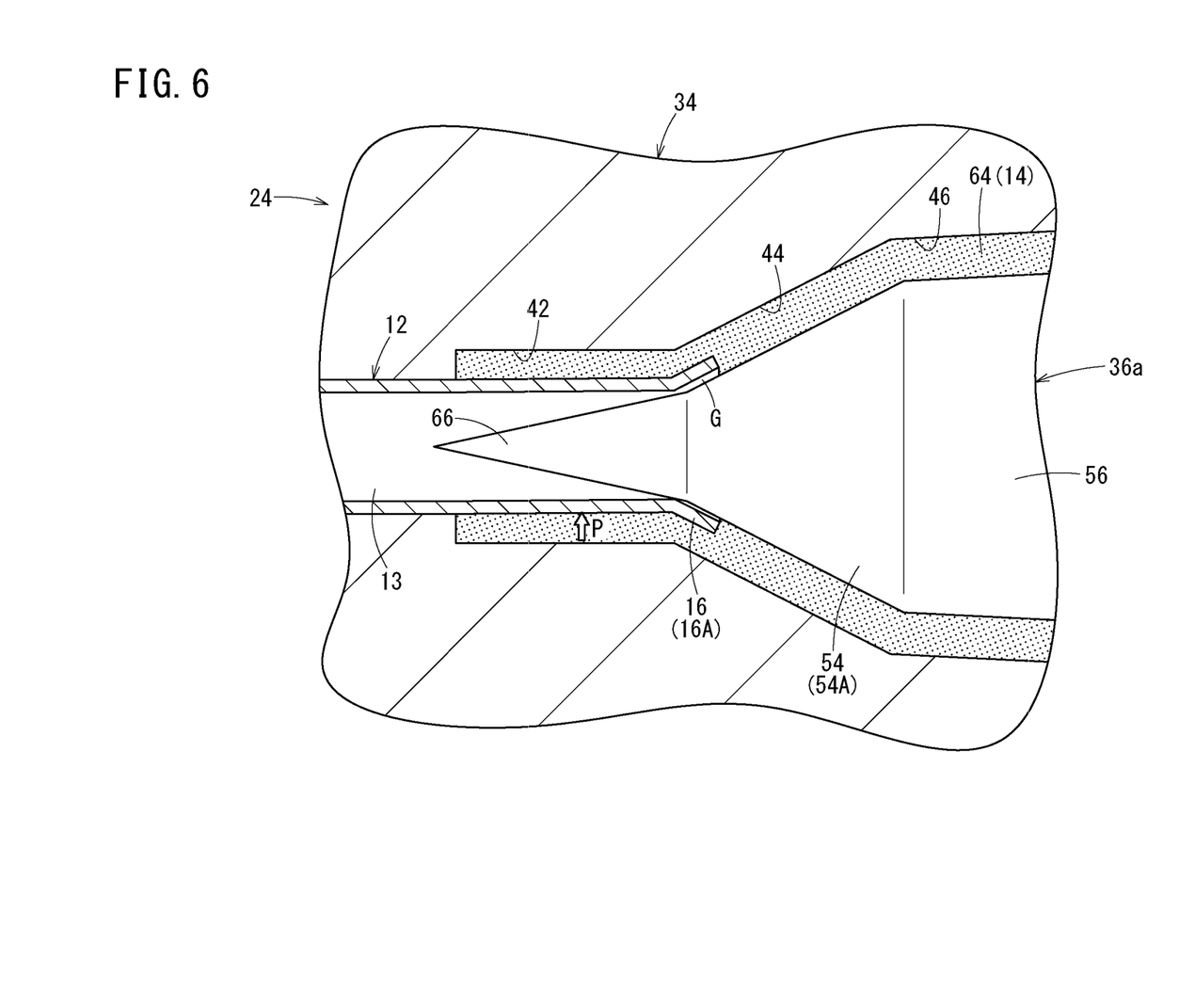
FIG. 6 is an explanatory diagram of an injection molding step when a core pin according to a modification is used.

Note that in the abovementioned manufacturing method of the medical needle 10 and the manufacturing apparatus 22, a core pin 36a according to a modification shown in FIG. 6 may be employed as an alternative to the core pin 36 having the straight distal insertion portion 52. This core pin 36a has such a tapered distal insertion portion 66 on a distal side of the tapered portion 54A that a diameter thereof decreases toward the distal direction. The abovementioned effects derived when the core pin 36 is employed to manufacture the medical needle 10 can be similarly obtained when the core pin 36a is employed.

Note, however, that employing the core pin 36, which has the straight distal insertion portion 52 can facilitate setting a flare processing condition width that enables the suppression of the generation of flashes to be larger than that when the core pin 36a, which has the tapered distal insertion portion 66 is employed. The reason is as follows.

When the core pin 36a is used, the inner surface of the proximal portion of the needle body 12 (inner surface closer to the distal side than the flare-shaped portion 16A) is not supported by the core pin 36a as the core pin 36 is moved backward; therefore, as shown in FIG. 6, if a resin pressure P acts on the needle body 12 from laterally thereof when the resin 64 is filled, the proximal portion of the needle body 12 becomes eccentric to the core pin 36a. Consequently, when the backward movement distance of the core pin 36 is equal to or larger than a certain degree, a relatively large gap and a relatively small gap are generated between the flare-shaped portion 16A and the core pin 36a and flashes are generated in a molded article if the resin 64 flows into the large gap. Due to this, it can be necessary to set the backward movement distance of the core pin 36a in the core-pin backward-movement in such a manner as not to generate such flashes.

On the other hand, as shown in FIG. 5, when the core pin 36 is used, even after the core pin 36 is moved backward by the core-pin backward-movement step, the distal insertion portion 52 having the straight portion 58 can support the inner surface of the proximal portion of the needle body 12 (inner surface closer to the distal side than the flare-shaped portion 16A). Due to this, even if the resin pressure acts on the needle body 12 from laterally thereof when the resin 64 is filled, the proximal portion of the needle body 12 does not become eccentric to the core pin 36. Therefore, when the core pin 36 is used, there is no constraint of the generation of flashes due to eccentricity; thus, it is possible to set the backward movement distance of the core pin 36 in the core-pin backward-movement step to be longer than that when the core pin 36a is used. That is, using the core pin 36 facilitates setting the flare processing condition width that helps enable the suppression of the generation of flashes to be larger than that when the core pin 36a is used.

The detailed description above describes a medical needle manufacturing method and a medical needle manufacturing apparatus for manufacturing a medical needle having a needle hub fixed to a proximal portion of a needle body by insert molding, and a medical needle. The invention is not limited, however, to the precise embodiments and variations described. Various changes, modifications and equivalents can effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A manufacturing method of a medical needle provided with a hollow metallic needle body and a resin needle hub fixed to a proximal portion of the needle body, the method comprising:
   a proximal end portion molding step of molding a proximal end portion in the proximal portion of the needle body by inserting a core pin of an injection molding mold into the proximal portion of the needle body and widening the proximal portion of the needle body;
   a core-pin backward-movement step of, after the molding of the proximal end portion, moving backward the core pin by a predetermined distance relatively to the needle body in such a manner that the proximal end portion springs back; and
   an injection molding step of, after the core-pin backward-movement step, molding the needle hub by injecting a resin into the injection molding mold while relative positions of the needle body and the core pin are held.

2. The manufacturing method of the medical needle according to claim 1, wherein the core-pin backward-movement step comprises moving backward the core pin relatively to the needle body in such a manner that a gap into which the resin cannot flow is formed between the proximal end portion and the core pin.

3. The manufacturing method of the medical needle according to claim 2, wherein the core pin includes a proximal end portion molding portion for molding the proximal end portion, and a support portion smaller in a diameter than the proximal end portion molding portion, extending from a distal end of the proximal end molding portion in a distal direction, inserted into the proximal portion of the needle body, and supporting the needle body from inside.

4. The manufacturing method of the medical needle according to claim 1, wherein the proximal end portion is a flare-shaped portion having a diameter increasing toward a proximal direction.

5. The manufacturing method of the medical needle according to claim 2, wherein the proximal end portion is a flare-shaped portion having a diameter increasing toward a proximal direction.

6. The manufacturing method of the medical needle according to claim 3, wherein the proximal end portion is a flare-shaped portion having a diameter increasing toward a proximal direction.

7. The manufacturing method of the medical needle according to claim 3, wherein the proximal end portion is a flare-shaped portion having a diameter increasing toward a proximal direction, and the proximal end portion molding portion is a tapered portion having an outer diameter decreasing toward the distal direction.

8. The manufacturing method of the medical needle according to claim 1, wherein the proximal end portion has a diameter larger than that of portions of the needle body distally of the proximal end portion.

9. The manufacturing method of the medical needle according to claim 1, wherein the core pin has a tapered portion, and an angle of an outer surface of the tapered portion of the core pin with respect to an axis of the core pin is 10° to 45°.

10. The manufacturing method of the medical needle according to claim 9, wherein the proximal end portion of the needle body after molding has been completed has a shape that matches the outer surface shape of the tapered portion of the core pin.

11. The manufacturing method of the medical needle according to claim 1, further comprising:
   before the proximal end molding step, inserting the proximal side of the needle body into a first insertion hole of a female mold in a state in which the proximal portion of the needle body protrudes into a cavity of the female mold by a predetermined length; and
   fixing the needle body to the female mold.

12. The manufacturing method of the medical needle according to claim 1, wherein the insertion of the core pin of the injection molding mold into the proximal portion of the needle body comprises:
   moving the core pin forward by 0.1 mm to 0.3 mm.

13. The manufacturing method of the medical needle according to claim 1, wherein the proximal end portion has a constant outer diameter, the constant outer diameter being larger than that of portions of the needle body distally of the proximal end portion.

14. The manufacturing method of the medical needle according to claim 1, wherein the backward movement of the core pin by the predetermined distance relatively to the needle body causes the proximal end portion to spring back from 0.01 mm to 0.1 mm, and wherein the predetermined distance is 0.03 mm to 0.08 mm.

15. The manufacturing method of the medical needle according to claim 1, wherein the needle body is made of one or more of the following:
   stainless steel, a cobalt chrome alloy, aluminum, an aluminum alloy, titanium, or a titanium alloy.

16. The manufacturing method of the medical needle according to claim 1, wherein the core pin has a straight distal insertion portion on a distal side of the core pin or a tapered distal insertion portion on the distal side of the core pin.

* * * * *